United States Patent [19]

Mueller, Jr.

[11] 3,944,343
[45] Mar. 16, 1976

[54] LIGHT INCLINING ACCESSORY FOR SLIT LAMP

[75] Inventor: Werner Mueller, Jr., North Easton, Mass.

[73] Assignee: Codman & Shurtleff, Inc., Randolph, Mass.

[22] Filed: Aug. 16, 1974

[21] Appl. No.: 498,238

[52] U.S. Cl. .................. 351/16; 350/292; 351/14; 351/39
[51] Int. Cl.² .................. A61B 3/10; G02B 5/08
[58] Field of Search ............ 350/7, 292; 351/14, 16, 351/39

[56] References Cited
UNITED STATES PATENTS

| | | | |
|---|---|---|---|
| 1,193,999 | 8/1916 | Dixon | 350/292 X |
| 3,161,885 | 12/1964 | Corcoran | 350/7 X |
| 3,433,560 | 3/1969 | Gambs | 351/14 |
| 3,830,562 | 8/1974 | McGraun et al. | 351/14 |

Primary Examiner—Paul A. Sacher
Attorney, Agent, or Firm—John J. Simkanich

[57] ABSTRACT

A light inclining accessory for a slit lamp includes a multi-faceted mirror having a top segment for receiving an illumination beam from the slit lamp and directing the illumination beam horizontally toward a focal point coinciding with the eye of a patient and a plurality of additional mirror segments having varying angles relative to each other, and a light directing device pivotally mounted on the slit lamp to be positioned to intercept the illumination beam and selectively adjustable to direct the illumination beam toward the additional mirror segments such that the illumination beam can be directed toward the focal point at various angles of inclination.

22 Claims, 4 Drawing Figures

LIGHT INCLINING ACCESSORY FOR SLIT LAMP

BACKGROUND OF THE INVENTION

1. Field of the Invention

The present invention pertains to slit lamps and, more particularly, to a light inclining accessory therefor for producing illumination beams at various inclinations below the horizontal.

2. Discussion of the Prior Art

Slit lamps are conventionally utilized by ophthalmologists to examine the human eye. Such slit lamps provide an illumination beam having a slit image of varying widths and include a microscope for examining the area of the eye illuminated by the beam. The illumination beam is normally directed toward the eye along a horizontal optical axis by reflection of a vertical illumination beam with a 45° reflecting mirror.

In many cases, such as to examine the anterior chamber behind the cornea and the vitreous, it is desired to illuminate the eye with a beam inclining relative to the horizontal. In the past, the inclination of the illumination beam of slit lamps has been accomplished by tilting or pivoting the entire illumination column or by the use of complex optics, such as prisms, integrally formed with the slit lamp. These methods of inclining the illumination beam suffer the disadvantages of being unwieldy and expensive.

SUMMARY OF THE INVENTION

Accordingly, it is an object of the present invention to overcome the disadvantages of the prior art by providing a system for inclining the illumination beam of a slit lamp in a simple and inexpensive manner.

The present invention is generally characterized in a light inclining accessory for a slit lamp having an illumination column providing an illumination beam from an end thereof and a mirror support spaced from the end of the illumination column, the accessory comprising a mirror adapted to be mounted on the mirror support and having a plurality of mirror segments arranged at varying angles relative to each other, and a light directing device adapted to be positioned between the end of the illumination column and the mirror to intercept the illumination beam and selectively direct the illumination beam toward the mirror segments whereby the illumination beam can be directed toward the eye of a patient at various angles of inclination.

Another object of the present invention is to provide an accessory for inclining the illumination beam of conventional slit lamps, which accessory can be simply and easily assembled on the slit lamps and can be swung out of the way without requiring disassembly when not in use.

A further object of the present invention is to utilize a multi-faceted mirror having mirror segments arranged at varying angles relative to each other to provide inclined illumination beams of substantially the same length.

The present invention has an additional object in that a slit lamp is provided with a light directing device pivotally mounted on a column and movable to intercept the illumination beam of the slit lamp to reflect the illumination beam toward a mirror to provide an inclined illumination beam toward a focal point, the light directing device including a mirror movable to direct the illumination beam at selected angles of inclination.

Yet another object of the present invention is to provide various inclined illumination beams for a slit lamp while maintaining the focal point of the beams at substantially the same position coincidental with the focal point of the slit lamp microscope.

Some of the advances of the present invention over the prior art are that the light inclining accessory of the present invention is inexpensive to produce and simple to assemble with conventional slit lamps, the mirror does not interfere with the optical axis of the slit lamp microscope and the angle of inclination desired can be easily selected by an operator.

Other objects and advantages of the present invention will become apparent from the following description of the preferred embodiment taken in conjunction with the accompanying drawings.

DESCRIPTION OF THE PREFERRED EMBODIMENT

Figure 1:
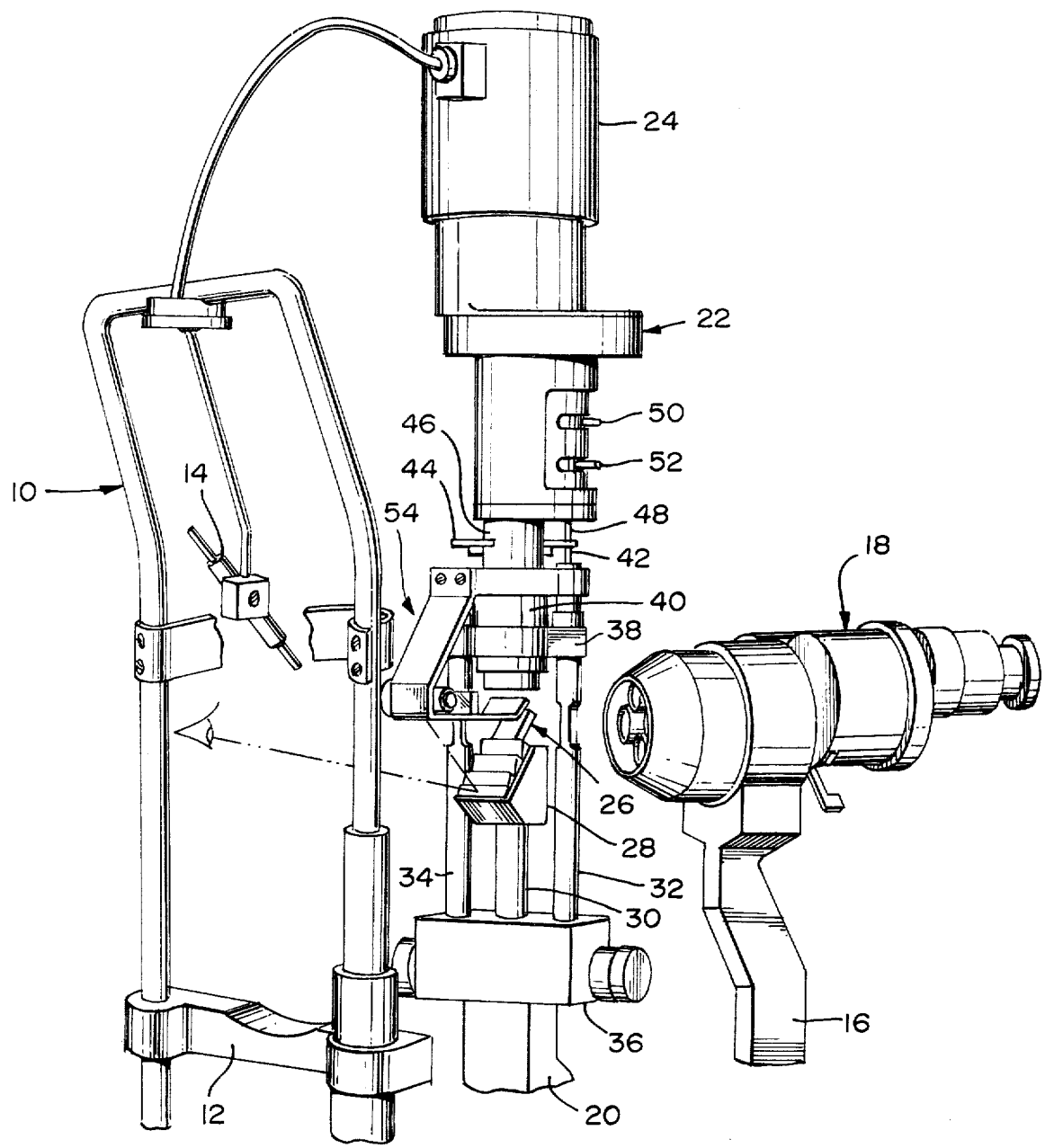
FIG. 1 is a broken perspective of a slit lamp utilizing a light inclining accessory according to the present invention.

A slit lamp utilizing a light inclining accessory according to the present invention is illustrated in FIG. 1 and includes a head rest frame 10 mounted on a table or other suitable support (not shown) with a chin support 12 extending between parallel uprights of the frame 10 and vertically adjustable to permit alignment of a patient's eye level. A fixation light 14 depends from the top of the head rest frame and is adapted to be positioned such that examination of a patient's eye is facilitated when the patient is looking at the fixation light.

The slit lamp conventionally includes a carriage, not shown, movable relative to the head rest frame 10 by means of a spherical element mounted in the carriage and riding on a surface, and a control lever, not shown, is conventionally provided to permit an operator to move the carriage horizontally to provide fine focus for the slit lamp. Mounted on the carriage is a pivot assembly, now shown, which is vertically adjustable and includes a microscope arm 16 carrying a binocular microscope 18 and an illumination arm 20 carrying a vertical illumination column 22, the arms 16 and 20 being pivotally mounted such that the microscope 18 and the illumination column 22 are independently pivotal about the same axis.

The illumination column 22 includes a lamp, not shown, mounted in a housing 24 and arranged to direct a vertical beam of light through a condenser assembly, not shown, to a mirror 26 mounted in a support 28 carried on a post 30 such that the mirror is in substantially horizontal alignment with the observation axis of the microscope 18 and has a portion oriented at substantially 45° C to the vertical to direct the illumination beam toward the eye of a patient. The illumination column 22 is supported on the illumination arm 20 by a pair of spaced columns 32 and 34 extending on opposite sides of mirror 26 between a combination control device 36 and a pair of ears 38 extending from a collar 40, and the post 30 is similarly supported on the combination control device 36. Column 32 has a central bore therein for slidably receiving a control rod 42 having an end abutting a flange 44 extending from a slidable member 46, and a control rod 48 has a lower end abutting flange 44 and an end extending within housing 24 to control a slit diaphragm assembly, not shown.

The illumination beam provided by the lamp passes through the slit formed by the slit diaphragm assembly and through an optical system and an objective in a bottom end 49 of the illumination column 22 to be deflected by the 45° portion of the mirror 26 toward a focal point coinciding with the eye of the patient. The optical system includes a filter assembly operable by a lever 50 to selectively position one of a plurality of filters in the path of the illumination beam, such filters including a normal light filter, a heat absorption filter, a 50% density filter, a blue-green cobalt filter and any other desired filters. The optical system also includes an aperture assembly operated by a lever 52 to position an aperture of selected size in the path of the illumination beam, such apertures desirably having sizes of 0.2mm, 1mm, 3mm, 4mm, 6mm, 8mm and 10mm. The optical system can be rotated to vertically or horizontally orient the slit image of the illumination beam.

With the exception of the mirror 26 and the combination control 36, the above described structure of the slit lamp is conventional; and, thus, a detailed description thereof has been omitted. However, reference is made to the MENTOR Slit Lamp marketed by Mentor Division of Codman & Shurtleff, Inc. and accompanying literature for more detailed structural and operational information relative to the above described structure and further reference is made to patent application Ser. No. 373,335 filed June 25, 1973 for more detailed discussion of the structure and operation of the combination control device 36 and the illumination column 22.

Conventionally, mirror 26 has lower and upper portions with the upper portion being of reduced width to permit viewing through the binocular microscope 18 and the lower and upper portions being coplanar at a 45° angle to the vertical illumination column to direct a slit image along a substantially horizontal optical axis to the eye of a patient, as shown in the aforementioned patent application Ser. No. 373,335.

Figure 2:
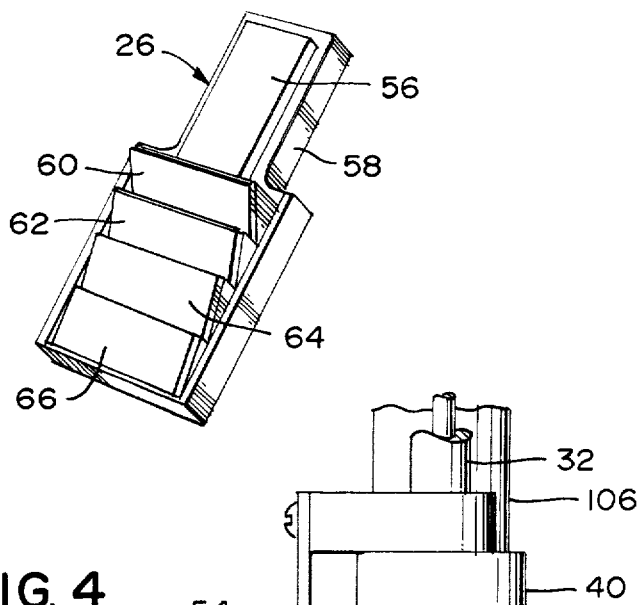
FIG. 2 is a perspective of the multi-faceted mirror of the light inclining accessory of the present invention.

In accordance with the present invention, a light inclining accessory is provided as an attachment for the slit lamp and includes two basic components, a multi-faceted mirror 26 and a light directing device 54. The multi-faceted mirror 26, as best shown in FIG. 2, is formed of a top mirror segment 56 mounted flat on a base 58 and mirror segments 60, 62, 64 and 66 mounted on the base at progressively greater angles to the plane of the base. The mirror 26 is mounted in the mirror support 28 by sliding the base 58 into a channel in the top of the support such that the top segment 56 is disposed at an angle of 45° to the illumination column and in axial alignment with the illumination beam to change the direction thereof from substantially vertical to substantially horizontal.

Figure 3:
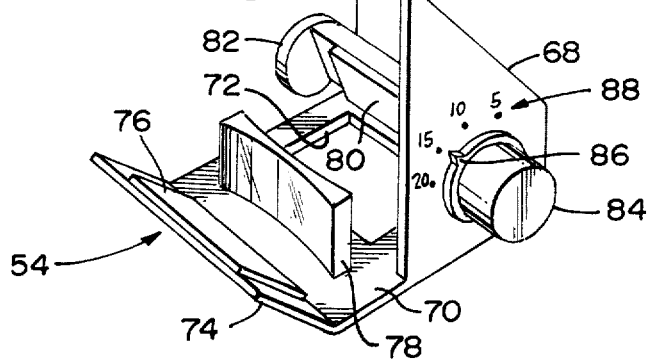
FIG. 3 is a perspective of the light directing device of the light inclining accessory of the present invention.

The light directing device 54 is best shown in FIG. 3 and includes a body 68 having a base 70 with a window 72 therein and an upturned lip 74 extending therefrom, preferably at an angle of 45°. A mirror 76 is mounted on lip 74 in order to bend the illumination beam 90° to pass through a double-concave, divergent lens 78 mounted on the base 70 and be reflected by a movable mirror 80 supported on an axle 82 rotatably mounted on a side wall of body 68. A knob 84 is secured to the hub of axle 82 and has a pointer 86 for indexing rotation of the mirror 80 with indicia 88 carried on the body 68. Rotation of mirror 80 is limited by abutment of a flange 90 extending from the axle with stops 92 and 94 on the inside of the side wall of body 68. A clamping member 96 extends transversely from the top edge of the front wall of body 68 and has a lug portion 98 on one side thereof with a bore 100 therethrough and a central portion 102 having a semi-circular recess 104 therein. The bore 100 has a diameter to slidably receive the column 32 and permit pivotal movement of the light directing device 54 thereabout. The recess 104 has a diameter substantially the same as that of a barrel 106 with the clamping member abutting the annular top shoulder of collar 40 to precisely axially position the light directing device. The body 68 can be of single or multi-part construction of any suitable material, such as plastic or metal; however, the clamping member 96 is preferably made of a flexible resilient material, such as plastic, to permit the light directing device to snap into place with the barrel firmly gripped by the clamping member.

In order to assemble the light inclining accessory with the slit lamp, the conventional mirror is removed from the channel in support 28 and mirror 26 is substituted therefor, and the flange 44 is raised to permit the clamping member 96 to be positioned such that the column 32 is received in bore 100. The assembly of the light inclining accessory with the slit lamp is now complete and the light directing device 54 can be pivoted about the column 32 from a rest position not interfering with the illumination beam supplied through the bottom end 49 of the illumination column to an operative position intercepting the illumination beam.

Figure 4:
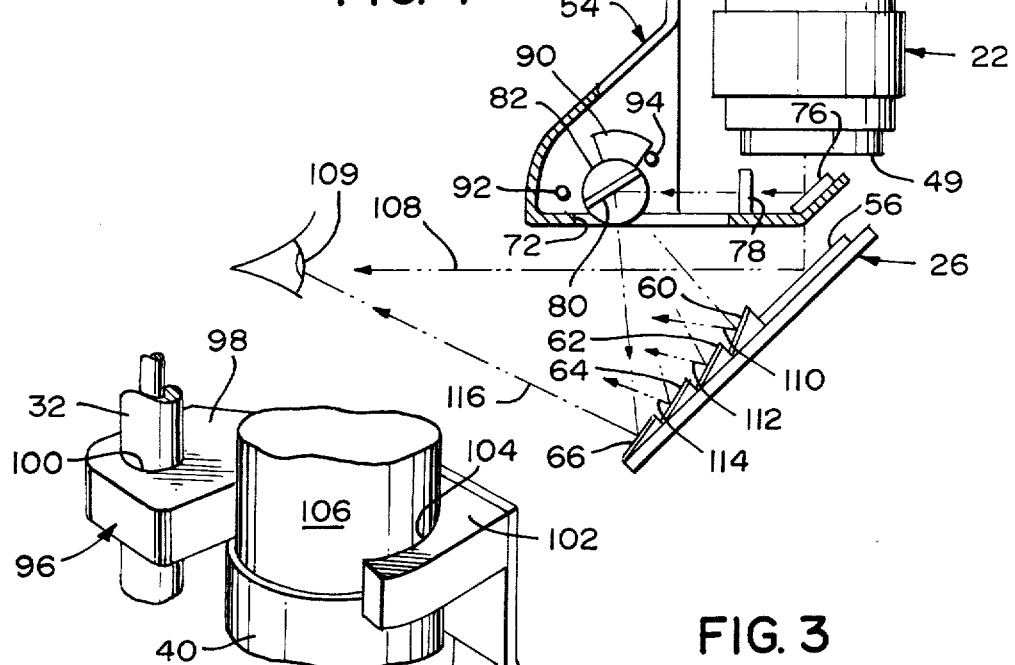
FIG. 4 is a schematic side elevation of the slit lamp with the light inclining accessory in position to direct light toward the eye of a patient at various incremental inclinations.

During normal operation of the slit lamp, the light directing device 54 is pivoted to its rest position such that the illumination beam from the illumination column 22 is reflected by top mirror segment 56 along a horizontal path indicated at 108 in FIG. 4 to the focal point 109 which coincides with the eye of the patient and the focal point of the binocular microscope 18. The reduced width of the top mirror segment 56 does not interfere with the optical viewing axis of the microscope 18 such that with the light directing device 54 in the rest position, operation of the slit lamp is conventional.

When it is desired to illuminate the eye of a patient with an inclined beam, the light directing device 54 is pivoted to its operative position, as shown in FIGS. 1, 3 and 4, such that the mirror 76 is positioned directly under the objective at the bottom end 49 of the illumination column. The mirror 76 is oriented at an angle of 45° to the vertical such that the illumination beam is reflected along a horizontal path through the divergent lens 78 to the movable mirror 80 where the illumination beam is reflected to be selectively directed toward one of the mirror segments 60, 62, 64 or 66. From the mirror segments 60, 62, 64 and 66, the illumination beam is reflected to the focal point 109 along paths 110, 112, 114, and 116 which are inclined relative to horizontal path 108 by 5°, 10°, 15° and 20°, respectively. Rotation of knob 84 permits the selection of the desired inclination of the illumination beam and, if desired, detent means can be provided to assure precise positioning of the movable mirror 80.

The mirror segments 60, 62, 64 and 66 are vertically displaced and the angular relationship therebetween is such that the angle with the vertical increases with descending vertical alignment of the mirror segments and with this arrangement of the mirror segments, the paths of the illumination beam from the movable mirror 80 to the focal point for each of the angles of inclination are of substantially the same distance. Since the length of travel of the illumination beam is increased for the inclined beams relative to the horizontal beam 108, the divergent lens 78 acts to compensate for the average increased distance by stretching the focal length thereby assuring that the illumination beam is focused at the focal point 109.

From the above, it will be appreciated that the light inclining accessory of the present invention is extremely advantageous due to its simplified structure and ease of assembly with existing slit lamps, and the light inclining accessory can be used with any suitable slit lamp, the above slit lamp description being provided for exemplary purposes only. Furthermore, if desired, the light inclining structure could be incorporated integrally with a slit lamp. Additionally, the light directing device 54 can be constructed to swing up, down or to the opposite side in its rest position, as desired, and can be supported on any suitable structure of the slit lamp. Similarly, while the relationship between the mirror segments 60, 62, 64 and 66 with the rotating mirror 80 is preferred due to the standardized focal length for the inclined illumination beams, the mirror could be movable linearly or in any other manner with suitable modification of the alignment of the facets of the mirror 26 to provide desired inclinations of the illumination beam. To this end, the angular orientation of the mirror segments or facets is dependent on the position and movement of the moveable mirror 80, in order to provide the desired inclinations of the illumination beam below the horizontal. That is, the angular orientation of each of the mirror segments is dependent on the horizontal and vertical spacing of the rotating mirror 80 from each of the mirror segments and the distance of each of the mirror segments from the focal point 109. The facets or segments of the mirror 26 can be formed integrally from a single piece of reflective material, such as by grinding glass or any other suitable manner.

Inasmuch as the present invention is subject to many variations, modifications and changes in detail, it is intended that all matter described above or shown in the accompanying drawings be interpreted as illustrative and not in a limiting sense.

What is claimed is:

1. A light inclining accessory of an ophthalmologic slit lamp having an illumination column providing an essentially vertical illumination beam from an end thereof, a support spaced from that end of the illumination column, and a binocular microscope for viewing a patient's eye, said accessory comprising:

first means adapted to be mounted on said support for reflecting said illumination beam essentially into the horizontal, said means accomplishing said reflection without converging or diverging the rays of said beam;

means for intercepting and redirecting said illumination beam, said intercepting and redirecting means being selectively positionable between said illumination column and said illumination beam first reflecting means, said intercepting and redirecting means being adjustable to selectively redirect said beam at one of various angles; and a plurality of means for reflecting said redirected beam into the eye of a patient at various angles of inclination, each of said redirected beam reflecting means being mounted on said support at varying angles relative to each other and to said illumination beam first reflecting means.

2. The apparatus of claim 1 wherein said intercepting and redirecting means includes:

second means for reflecting said illumination beam essentially into the horizontal, said means accomplishing said reflection without converging or diverging the rays of said beam, said means being positionable between said illumination column and said illumination beam first reflecting means; and means for selectively directing said reflected beam from said illumination beam second reflecting means towards said plurality of redirected beam reflecting means.

3. The apparatus of claim 2 wherein said illumination beam first reflecting means, said illumination beam second reflecting means, said selectively directing means, and said plurality of redirected beam reflecting means are flat mirrors.

4. The apparatus of claim 3 wherein said selectively directing mirror directs said reflected beam selectively to only one of said plurality of redirected beam reflecting mirrors.

5. The apparatus of claim 4 wherein said selectively directing mirror is pivotal about a fixed point, said pivoting governing the selective direction to only one of said plurality of redirected beam reflecting mirrors.

6. The apparatus of claim 5 also including means for diverging in a horizontal direction the reflected beam from said illumination beam second reflecting mirror, said means being positioned between said illumination beam second reflecting mirror and said reflected beam selectively directing pivotal mirror.

7. The apparatus of claim 6 wherein said diverging means includes a double concave lens.

8. The apparatus of claim 7 wherein said illumination beam second reflecting mirror, said double concave lens and said selectively directing pivotal mirror are mounted upon a plate.

9. The apparatus of claim 8 wherein said plate is mounted to said illumination column with a clamping member, said clamping member having a semicircular recess therein and being of flexible resilient material so as to permit snapping into place on and rotation about said illumination column.

10. The apparatus of claim 9 wherein said plate includes a mount capable of supporting and pivoting said selectively directing pivotal mirror; and an opening through said plate in proximity to said pivotal mirror mount.

11. The apparatus of claim 10 wherein said illumination beam second reflecting mirror is narrower than said illumination beam first reflecting mirror.

12. A slit lamp comprising:

a substantially vertical illumination column having a bottom end for providing an illumination beam;

mirror means spaced below said bottom end of said illumination column including a top mirror segment directly aligned with said illumination beam and arranged at an angle of 45° to the vertical to bend said illumination beam 90° without converging or diverging the rays of said beam for directing along a horizontal path to a focal point, said mirror means further including at least one additional mirror segment disposed below said top mirror segment; and light directing means for intercepting said illumination beam and directing said illumination beam without converging or diverging the rays of said beam toward said additional mirror segment, said light directing means being pivotally mounted on said illumination column to be moved from a rest position not interfering with passage of said illumination beam to said top mirror segment to an operative position between said bottom end of said illumination column and said top mirror segment to direct said illumination beam toward said additional mirror segment whereby said illumination beam can be directed toward the focal point at an inclined angle to the horizontal.

13. A slit lamp as recited in claim 12 wherein said mirror means includes a plurality of additional mirror segments disposed below said top mirror segment and arranged at varying angles relative to each other and said light directing means includes a mirror movable to selectively direct light toward said additional mirror segments.

14. A slit lamp as recited in claim 13 wherein said light directing means includes a mirror disposed at 45° to the vertical for intercepting said illumination beam and directing said illumination beam toward said movable mirror.

15. A slit lamp as recited in claim 14 wherein said movable mirror is rotatable and said light directing means includes divergent lens means between said intercepting mirror and said movable mirror.

16. A slit lamp as recited in claim 13 wherein said additional mirror segments are arranged such that the paths of said illumination beam from said movable mirror to said focal point are of substantially the same distance.

17. A slit lamp as recited in claim 12 wherein said illumination column includes a barrel, a collar surrounding said barrel and a column disposed in spaced parallel relation to said barrel, and said light directing device includes a clamping member slidably receiving said column to be pivotal thereabout and carrying means for clamping said barrel and abutting said collar to position said light directing device relative to the bottom end of said illumination column.

18. A method of providing a beam of light at an angle of incidence from the horizontal in a slit lamp ophthalmologic device having a vertical slit lamp column, a horizontal viewing binocular microscope and a mirror for reflecting the illumination beam from said column essentially in a horizontal plane into a patient's eye, comprising the steps of:

intercepting said beam before it hits said reflecting mirror;

reflecting said beam in a horizontal plane above its previous normal plane of reflection from said reflecting mirror;

redirecting said reflected beam at various angles; and reflecting said redirected beam into said patient's eye at an angle of incidence with the horizontal.

19. The method of claim 18 wherein said intercepting said beam reflecting said beam, redirecting said reflected beam and reflecting said redirected beam are accomplished without converging or diverging the rays of said beams.

20. The method of claim 19 wherein the step of redirecting said reflected beam occurs selectively at one of said various angles.

21. The method of claim 20 wherein the step of reflecting said redirected beam into said patient's eye occurs at different angles of incidence to the horizontal, said angle of incidence being a function of said selected redirected angle.

22. The method of claim 21 also including after the step of reflecting said beam in a horizontal plane, the step of diffusing said reflected beam.

* * * * *

UNITED STATES PATENT AND TRADEMARK OFFICE
CERTIFICATE OF CORRECTION

PATENT NO. : 3,944,343
DATED : March 16, 1976
INVENTOR(S) : Werner Mueller, Jr.

It is certified that error appears in the above-identified patent and that said Letters Patent are hereby corrected as shown below:

In Column 2, Line 51, the word "now shown" should read --- not shown ---.

In Column 2, Line 65, the word "45°C" should read --- 45° ---.

$Signed and Sealed this$

Fourteenth Day of September 1976

[SEAL]

*Attest:*

RUTH C. MASON
*Attesting Officer*

C. MARSHALL DANN
*Commissioner of Patents and Trademarks*